US008835513B2

(12) United States Patent
Sargeant et al.

(10) Patent No.: US 8,835,513 B2
(45) Date of Patent: *Sep. 16, 2014

(54) DRUG DELIVERY DEVICES

(75) Inventors: Timothy Sargeant, Hamden, CT (US);
Joshua Stopek, Guilford, CT (US);
Ahmad Robert Hadba, Middlefield, CT (US)

(73) Assignee: Covidien LP, Mansfield, MA (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/299,978

(22) Filed: Nov. 18, 2011

(65) Prior Publication Data

US 2012/0076773 A1 Mar. 29, 2012

Related U.S. Application Data

(63) Continuation-in-part of application No. 12/788,933, filed on May 27, 2010, now Pat. No. 8,349,349, which is a continuation-in-part of application No. 11/712,333, filed on Feb. 28, 2007, now Pat. No. 7,858,079.

(60) Provisional application No. 60/777,297, filed on Feb. 28, 2006.

(51) Int. Cl.
*A61K 47/48* (2006.01)
*A61K 31/00* (2006.01)
*A61K 31/715* (2006.01)
*A61K 38/22* (2006.01)
*A61K 38/18* (2006.01)
*A61K 38/43* (2006.01)
*A61L 24/04* (2006.01)
*A61L 24/00* (2006.01)
*A61L 27/54* (2006.01)
*A61L 27/34* (2006.01)
*A61L 31/10* (2006.01)
*A61L 31/16* (2006.01)
*C09J 189/00* (2006.01)
*A61L 33/00* (2006.01)
*A61L 24/10* (2006.01)

(52) U.S. Cl.
CPC ....... *A61L 24/0031* (2013.01); *A61L 2300/406* (2013.01); *A61L 2300/42* (2013.01); *A61L 2300/608* (2013.01); *A61L 27/54* (2013.01); *A61L 31/10* (2013.01); *A61L 33/0011* (2013.01); *A61L 24/108* (2013.01); *A61L 2300/416* (2013.01); *A61L 24/043* (2013.01); *A61L 31/16* (2013.01); *A61L 27/34* (2013.01); *C09J 189/00* (2013.01)
USPC ............ 514/772.1; 514/9.7; 514/7.6; 514/54; 424/94.1

(58) Field of Classification Search
USPC .................. 514/7.6, 9.7, 54, 772.1; 424/94.1
See application file for complete search history.

(56) References Cited

U.S. PATENT DOCUMENTS

| 4,359,049 | A | 11/1982 | Redl et al. |
| 4,874,368 | A | 10/1989 | Miller et al. |
| 4,978,336 | A | 12/1990 | Capozzi et al. |
| 4,979,942 | A | 12/1990 | Wolf et al. |
| 5,368,563 | A | 11/1994 | Lonneman et al. |
| 6,333,051 | B1 | 12/2001 | Kabanov et al. |
| 6,527,749 | B1 | 3/2003 | Roby et al. |
| 6,632,929 | B1 | 10/2003 | Wilchek et al. |
| 6,638,508 | B2 | 10/2003 | Schechter et al. |
| 6,648,922 | B2 | 11/2003 | Ung-Chhun et al. |
| 7,858,079 | B2 * | 12/2010 | Hadba et al. ............... 424/78.27 |
| 8,349,349 | B2 * | 1/2013 | Sargeant et al. ............. 424/423 |
| 2002/0022266 | A1 | 2/2002 | Wagner et al. |
| 2002/0128234 | A1 | 9/2002 | Hubbell et al. |
| 2003/0022216 | A1 | 1/2003 | Mao et al. |
| 2003/0153001 | A1 | 8/2003 | Soane et al. |
| 2003/0181423 | A1 | 9/2003 | Clapper et al. |
| 2004/0023413 | A1 | 2/2004 | Opalsky |
| 2005/0244453 | A1 | 11/2005 | Stucke et al. |
| 2005/0281802 | A1 | 12/2005 | Gong et al. |
| 2010/0285088 | A1 | 11/2010 | Sargeant et al. |

FOREIGN PATENT DOCUMENTS

| WO | WO 94/23759 A1 | 10/1994 |
| WO | WO 01/06829 | 2/2001 |
| WO | WO 01/06829 A2 | 2/2001 |
| WO | WO 03/000234 | 1/2003 |
| WO | WO 2006/063249 A2 | 6/2006 |
| WO | WO 2007/100882 A2 | 9/2007 |
| WO | WO 2011/011347 A2 | 1/2011 |

OTHER PUBLICATIONS

European Search Report for EP 07751965.0-1219 date of completion is Aug. 20, 2012 (11 pages).
Huang et al., "Biotin-Derivatized Poly(L-lysine)-g-poly(ethylene glycol): A Novel Polymeric Interface for Bioaffinity Sensing", Langmuir et al., 2002, 18, pp. 220-230.
Jia, Z. et al., "Functional Disulfide-Stabilized Polymer-Protein Particles", *Biomacromolecules*, vol. 10, pp. 3253-3258 (2009).
International Search Report from corresponding EP Appl. No. 12192946.7 mailed Feb. 1, 2013.
Xie et al., Synthesis and characterization of novel biotinylated biodegradable poly(ethylene glycol) -b-poly(carbonate-lactic acid) copolymers, QActa Biomaterialia, 1, 2005, pp. 635-641.
Huang et al., Biotin-Derivatized Poly(L-lysine)-g-poly(ethylene glycol): A Novel Polymeric Interface for Bioaffinity Sensing, Langmuir et al., 2002, 18, pp. 220-230.
Salmaso et al. Biochim. Biophys, Acta 1726, 57-66 (2005), available on line May 16, 2005.
Pardridge et al., Pharm. Res. vol. 15, No. 4, 576-582 (1998).

* cited by examiner

Primary Examiner — Chih-Min Kam

(57) ABSTRACT

Compositions provided by contacting a biotin-containing component and an avidin-containing component are useful as drug delivery devices. Bioactive agents may be covalently bound to the biotin-containing component, the avidin-containing component, or both, mixed therewith, or combinations of the foregoing.

16 Claims, No Drawings

DRUG DELIVERY DEVICES

CROSS-REFERENCE TO RELATED APPLICATIONS

This application is a continuation-in-part of U.S. patent application Ser. No. 12/788,933 filed May 27, 2010, now U.S. Pat. No. 8,349,349 which, in turn, is a continuation-in-part of U.S. patent application Ser. No. 11/712,333, filed Feb. 28, 2007, now U.S. Pat. No. 7,858,079, which claims priority to, and the benefit of, U.S. Provisional Patent Application No. 60/777,297 filed Feb. 28, 2006, the entire disclosures of each of which are incorporated by reference herein.

TECHNICAL FIELD

The present disclosure relates to compositions containing macromers capable of forming a matrix and the use of compositions containing these macromers as surgical adhesives or sealants, or drug delivery devices.

DESCRIPTION OF RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, preferably a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material is frequently observed.

It would be desirable to provide a biological adhesive and/or sealant that is fully synthetic and therefore highly consistent in its properties without the concern of viral transmission. Such a composition should be flexible and biocompatible and should be suitable for use as an adhesive or sealant.

SUMMARY

The present disclosure provides compositions suitable for use as drug delivery devices. In embodiments, a drug delivery device of the present disclosure may include a biocompatible biotin-containing component including a first polymer such as polyethylene glycols and absorbable polymers; a biocompatible avidin-containing component including a second polymer such as polyethylene glycols and absorbable polymers; and at least one bioactive agent, wherein the at least one bioactive agent is bound to the biotin-containing component, the avidin-containing component, or both, and wherein the drug delivery device releases the at least one bioactive agent in vivo.

The same or different bioactive agent(s) may be released from a drug delivery device of the present disclosure. The mechanism by which the bioactive agent is combined with the drug delivery device and/or components thereof may result in a drug delivery device having multiple release profiles of the same or different bioactive agent(s).

DETAILED DESCRIPTION

The present disclosure relates to a composition for use as a drug delivery device. The composition can be applied to living tissue and/or flesh of animals, including humans. The composition may also act as a tissue adhesive or sealant, which is biocompatible and non-immunogenic. The composition can be employed to adhere tissue edges, seal air/fluid leaks in tissues, adhere medical devices to tissue, and for tissue augmentation such as sealing or filling voids or defects in tissue.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

The composition of the present disclosure includes a component having at least one biotin group, or a derivative thereof, and a component having at least one avidin group, or a derivative thereof. The biotin moiety on the one component and the avidin group on the other component bond to one another thereby providing the present compositions. When the two components are combined, the composition rapidly forms a three dimensional gel-like adhesive matrix. Each component is preferably synthetic to reduce or eliminate immuno-reactions in a subject's tissue.

In embodiments, the composition of the present disclosure can act as a drug carrier or delivery device for bioactive agents, allowing controlled release and direct delivery of a drug or other bioactive agent to a specific location in an animal, especially a human. The bioactive agent may be combined with the biotin component, the avidin component, or both, or bound to the biotin-containing component, the avidin-containing component, or both. In other embodiments, the bioactive agent may be combined with the composition formed by the reaction of the biotin-containing component and the avidin-containing component, either during or after formation of the composition of the present disclosure.

Biotin (also known as vitamin H, coenzyme R) is a readily water-soluble substance found at low concentrations in blood and tissues. Biotin acts as a carrier of activated $CO_2$ and permits the transfer of $CO_2$ to acceptors without the need for additional free energy. Activated carboxybiotin is usually attached to an enzyme that is required for the formation of carboxybiotin. For example, biotin may be attached to pyruvate carboxylase which, in the presence of acetyl CoA, catalyzes the formation of carboxybiotin and the subsequent transfer of the activated carboxyl group to pyruvate, to form oxaloacetate.

The biotin-containing component can be any biocompatible compound that includes one or more biotin moieties. The compound can be any small molecule or polymer capable of being functionalized. The biotin-containing component can be bioabsorbable or non-bioabsorbable. In some embodiments, the biotin-containing component may be derived from a polysaccharide. Suitable polysaccharides include, for example, sorbitol, mannitol, sucrose, dextran, cyclodextrin, combinations thereof, and the like. In other embodiments, the biotin-containing component may be derived from a polyalkylene oxide ("PAO"). Suitable PAOs include, but are not limited to, polyethylene glycol ("PEG"), polyethylene oxide ("PEO"), polypropylene oxide ("PPO"), a polyethylene glycol with lactide linkages, polypropylene glycol ("PPG"), co-polyethylene oxide lock or random copolymers, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Various forms of PAOs, including functionalized PEGs, are also commercially available from providers which include, for example, Shearwater Polymers, Inc., Huntsville, Ala., and Texaco Chemical Company, Houston, Tex. In embodiments, combinations of the foregoing PAOs may be utilized.

In some embodiments, the biotin-containing component includes a bioabsorbable polymer. A bioabsorbable polymer breaks down in the body and may be gradually absorbed or eliminated by the body by hydrolysis, metabolic processes, or bulk or surface erosion. Examples of bioabsorbable materials suitable for making the biotin-containing component include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, polyamino acids (including, but not limited to, polyglutamic acid, polyaspartic acid, and synthetic amino acids with pendant acidic groups, including those commercially available from Sigma-Aldrich (St. Louis, Mo.), absorbable cyanoacrylates, poly(trimethylene carbonate), poly(iminocarbonate), copoly(ether-esters), polyalkylene oxalates, polyphosphazenes, polyiminocarbonates, and aliphatic polycarbonates. In some embodiments, combinations of the foregoing bioabsorbable materials may be utilized. For example, one or more of the foregoing absorbable polymers can be reacted with a PAO to provide a degradable polymer having hydrophilic properties which then can be functionalized with biotin to provide the biotin-containing component.

In some embodiments the biotin-containing component may be modified to produce a multi-functional material, i.e., one having a branched or star configuration. Methods for achieving branching are within the purview of those skilled in the art and include, for example, reacting the compound used to form the biotin-containing component with a multifunctional branching agent either prior to or after functionalization with biotin. Suitable multifunctional branching agents include, but are not limited to, tris(hydroxymethyl)aminomethane (also known as 2-amino-2-(hydroxymethyl)-1,3-propanediol), enterodiol, cyclodextrins, polysaccharides (e.g., sorbitols, mannitols, sucrose, dextrans, cyclodextrins, etc.) polyols, polyvinyl alcohols, combinations thereof, and the like.

In embodiments, the molecular weight of the biotin-containing component may be from about 200 to about 50,000, and in embodiments from about 500 to about 5,000.

Polymers and other compounds (e.g., macromers, oligomers, and/or small molecules) can be functionalized with biotin, i.e., biotinylated, according to any method within the purview of those skilled in the art. For example, PEG can be functionalized using those methods disclosed in Chapter 22 of Poly(ethylene Glycol) Chemistry: Biotechnical and Biomedical Applications, J. Milton Harris, ed., Plenum Press, N.Y. (1992).

In embodiments, the biotin-containing component includes a three part molecule containing a macromolecule or polymer, at least one biotin group, and at least one bioactive agent. The macromolecule may include both natural and synthetic biodegradable materials, as well as combinations thereof.

Representative natural biodegradable macromolecules include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Representative synthetic biodegradable macromolecules which may be utilized include polyhydroxy acids prepared from lactone monomers such as glycolide, lactide, caprolactone, ε-caprolactone, valerolactone, and δ-valerolactone; carbonates (e.g., trimethylene carbonate, tetramethylene carbonate, and the like); dioxanones (e.g., 1,4-dioxanone and p-dioxanone); 1,dioxepanones (e.g., 1,4-dioxepan-2-one and 1,5-dioxepan-2-one); and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactic-co-glycolic acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

The macromolecules may be functionalized to provide reactive sites to attach at least one bioactive agent, and/or the biotinylated end group. In embodiments, the macromolecule may be functionalized with a biotinylated bioactive agent. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly(P-Dioxanone), and copolymers thereof); and thiols may be provided on some proteins. Alternatively, the macromolecules may be functionalized with tissue or substrate binding end groups, such as poly(lactic acid) and/or poly(glycolic acid), which include terminal carboxyl or hydroxyl groups. The inclusion of tissue and/or substrate binding end groups may be desirable where the composition of the present disclosure is utilized as a coating for a medical device, or where anchoring a drug delivery device including a composition of the present disclosure to a specific location in the body is desired.

In embodiments, a bioactive agent, and/or the biotinylated reactive end group, as well as any tissue or substrate binding end group, may be conjugated to the macromolecule through the use of a linking agent. For amine containing macromolecules, for example, isothiocyanates, isocyanates, acyl azides, N-hydroxysuccinimide (NHS) and sulfo-NHS esters, sulfonyl chlorides, aldehydes and glyoxals, epoxides and oxiranes, carbonates, arylating agents, imidoesters, carbodiimides, and anhydrides may be utilized. For carboxyl containing macromolecules, for example, diazoalkanes and diazoacetyl compounds may be utilized, as well as carbonyldiimidazoles, carbodiimides, and NHS, which convert carboxylic acid into a reactive intermediate which is susceptible to reaction with amines or alcohols. For hydroxyl containing macromolecules, for example, epoxides and oxiranes, acyl azides, carbonyldiimidazole, disuccinimidyl carbonate and hydroxysuccinimidyl chloroformate, alkyl halogens, isocyanates, and methacryloyl or acryloyl chloride may be utilized, as well as oxidation with periodate and enzymatic oxidation.

In embodiments, the linking agent may form degradable groups between the macromer and bioactive agent, thereby providing a mechanism for the release of the bioactive agent in vivo (i.e., hydrolysis or other degradation of the degradable group).

In some embodiments, the bioactive agent may be conjugated to the macromolecule via succinimidyl esters such as NHS and sulfo-NHS; isocyanates and isothiocyanates; aldehydes such as oxidized starch, oxidized dextran, and oxidized PEG; and by Michael's Addition of acrylates which react with thiol groups.

For example, a PEG or similar macromer (for example, a 4 arm star) that has at least some of its arms terminated with NHS groups may be reacted with a linear $NH_2$-PEG-biotin to produce a PEG star having at least some of its arms terminated with biotin. At the same time, other arms of the macromer may be functionalized with a bioactive agent, in embodiments a biotinylated bioactive agent, possessing a group capable of reacting with the free arm of the macromer. Once formed, the new PEG star may be reacted with avidin to allow for avidin/biotin binding, resulting in cross-linked network (that is also hydrolysable) following intimate mixing of the two chemical solutions (in aqueous media). The bioactive agent bound to the macromer may then be released after degradation of the composition of the present disclosure and/or hydrolysis of any degradable linkage included in the arm of the macromer possessing the bioactive agent.

Biotin is commercially available with different functional groups, such as amine, sulfhydryl, carbonyl, and carboxy reactive chemistries. It is envisioned that a suitable commercially available functionalized biotin may be chosen based upon the macromolecule to which it is to be bound.

The avidin-containing component can be any biocompatible compound that has been functionalized with avidin, streptavidin or their derivatives. Thus, as used herein, an avidin-containing component can include one or more moieties derived from avidin, streptavidin or their derivatives. The compound can be any small molecule or a polymer capable of being functionalized. The avidin-containing component can be bioabsorbable or non-bioabsorbable.

Avidin (a glycoprotein from chicken egg white) and streptavidin (from *Streptomyces avidinii*) are two related proteins that bind biotin with similar dissociation constants of about $10^{-15}$ M. Avidin occurs naturally in a tetrameric form with four identical subunits, each having about 128 amino acid residues, six mannose residues, and three glucosamine residues, for a combined molecular weight of approximately 68,000. In addition to the ability of avidin and streptavidin to bind biotin, many of their physical properties are quite similar. Both, for example, are constructed of four non-covalently attached identical subunits, each of which bears a single biotin-binding site. Thus, each avidin or streptavidin can bind to four biotins. The subunit Mr values are very similar. Moreover, several short stretches in the sequences of the two proteins are preserved, particularly two Trp-Lys stretches that occur at approximately similar positions.

Avidin, streptavidin and their derivatives, as well as methods for obtaining the same, are within the purview of those skilled in the art. For example, modified avidins have been prepared, such as N-acyl avidins, e.g., N-formyl, N-acetyl and N-succinyl avidins. These derivatives of avidin reduce the charge of the protein, but they may all be prepared via covalent attachment to the available lysines of avidin. An alternative to lysine modification is the modification of arginines on avidin. In this case, the lysines are still available for subsequent interaction. Two different derivatives of avidin which are modified in this manner are commercially available. One, ExtrAvidin®, can be obtained in various functionally derivatized or conjugated forms from Sigma Chemical Company (St. Louis, Mo.). A second, NeutraLite Avidin™ (a product of Belovo Chemicals, Bastogne, Belgium), is a deglycosylated form of avidin obtained enzymatically, which exhibits a neutral pH and bears free lysine groups for further derivatization. Other avidin derivatives include those disclosed in U.S. Pat. Nos. 6,638,508 and 6,632,929, the entire disclosures of each of which are incorporated by reference herein.

In some embodiments, the avidin-containing component may be derived from a polysaccharide. Suitable polysaccharides include, for example, sorbitol, mannitol, sucrose, dextran, cyclodextrin, and the like, and combinations thereof. In other embodiments, the avidin-containing component may be derived from a polyalkylene oxide ("PAO"). Suitable PAOs include, but are not limited to, polyethylene glycol ("PEG"), polyethylene oxide ("PEO"), polypropylene oxide ("PPO"), a polyethylene glycol with lactide linkages, polypropylene glycol ("PPG"), co-polyethylene oxide lock or random copolymers, and poloxamers such as polyethylene oxide (PEO) copolymers with polypropylene oxide (PPO) such as the triblock PEO-PPO copolymers commercially available as PLURONICS® from BASF Corporation (Mt. Olive, N.J.). Various forms of PAOs, including functionalized PEGs, are also commercially available from providers which include, for example, Shearwater Polymers, Inc., Huntsville, Ala., and Texaco Chemical Company, Houston, Tex. In embodiments, combinations of the foregoing PAOs may be utilized.

In some embodiments, a bioabsorbable polymer is used to prepare the avidin-containing component. A bioabsorbable polymer breaks down in the body and may be gradually absorbed or eliminated by the body by hydrolysis, metabolic processes, or bulk or surface erosion. Examples of bioabsorbable materials suitable for making the avidin-containing component include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, polyamino acids (including, but not limited to, polyglutamic acid, polyaspartic acid, and synthetic amino acids with pendant acidic groups, including those commercially available from Sigma-Aldrich (St. Louis, Mo.), absorbable cyanoacrylates, poly(trimethylene carbonate), poly(iminocarbonate), copoly(ether-esters), polyalkylene oxalates, polyphosphazenes, polyiminocarbonates, and aliphatic polycarbonates. In some embodiments, combinations of the foregoing bioabsorbable materials may be utilized. For example, one or more of the foregoing absorbable polymers can be reacted with a PAO to provide a degradable polymer having hydrophilic properties which then can be functionalized with avidin to provide the avidin-containing component.

In some embodiments the avidin-containing component may be modified to produce a multi-functional material, i.e., one having a branched or star configuration. Methods for achieving branching are within the purview of those skilled in the art and include, for example, reacting the compound used to form the avidin-containing component with a multifunctional branching agent either prior to or after functionalization with avidin. Suitable multifunctional branching agents include, but are not limited to, tris(hydroxymethyl)aminomethane (also known as 2-amino-2-(hydroxymethyl)-1,3-propanediol), enterodiol, polysaccharides (e.g., sorbitols, mannitols, sucrose, dextrans, cyclodextrins, etc.) polyols, polyvinyl alcohols, combinations thereof, and the like.

In embodiments, the molecular weight of the avidin-containing component may be from about 200 to about 50,000, and in embodiments from about 500 to about 5,000.

Polymers and other compounds (e.g., small molecules) can be functionalized with avidin using any method within the purview of those skilled in the art. For example, PEG can be functionalized using those methods disclosed in Chapter 22 of Poly(ethylene Glycol) Chemistry: Biotechnical and Biomedical Applications, J. Milton Harris, ed., Plenum Press, NY (1992).

In embodiments, the avidin-containing component includes a three part molecule containing a macromolecule or polymer, a bioactive agent, and an avidinylated end group. The macromolecule may include both natural and synthetic biodegradable materials, as well as combinations thereof, which may include or may be functionalized with bioactive agents as described above. In other embodiments, tissue or substrate binding reactive groups may also be included on the avidin-containing component. The inclusion of tissue and/or substrate binding end groups may be desirable where the composition of the present disclosure is utilized as a coating for a medical device, or where anchoring a drug delivery device including a composition of the present disclosure to a specific location in the body is desired.

Avidin is a protein which includes free amines and carboxyl groups for reaction. It is envisioned that a suitable functionalized macromolecule may be employed for binding to the amine or carboxyl groups of avidin.

Each avidin or streptavidin binds one molecule of biotin. The unique feature of this binding is the strength and specificity of formation of the avidin-biotin complex. The resultant affinity constant, estimated at $1.6 \times 10^{15}$ $M^{-1}$ for avidin and $2.5 \times 10^{13}$ $M^{-1}$ for streptavidin, is the highest known for a protein and an organic ligand. It is so strong that biotin cannot be released from the binding site, even when subjected to a variety of drastic conditions such as high concentrations of denaturing agents at room temperature, e.g., 6 M guanidinium hydrochloride, 3 M guanidinium thiocyanate, 8 M urea, 10% β-mercaptoethanol or 10% sodium dodecyl sulfate. Under combined treatment with guanidinium hydrochloride at low pH (1.5) or upon heating (>70° C.) in the presence of denaturing agents or detergents, the protein may be denatured, and biotin can be dislodged from the disrupted binding site.

The biotin-containing component and the avidin-containing component may be prepared and stored separately prior to use. The biotin-containing component and/or the avidin-containing component can be stored neat. Alternatively, the biotin-containing component and/or the avidin-containing component can be stored as a dry powder that may be reconstituted (e.g., by mixing with water or other biocompatible solvent) immediately prior to use. Alternatively, the biotin-containing component and/or the avidin-containing component can be formulated into compositions containing water or some other biocompatible solvent and stored separately until application. For example, these formulations can be solutions, emulsions, and dispersions. The concentrations of the biotin-containing component and the avidin-containing component in such formulations will vary depending upon a number of factors, including the types and molecular weights of the components, including any polymers or macromers that are a part thereof, and the desired end use application. In embodiments, the biotin-containing component and/or the avidin-containing component may be present in such formulations in amounts from about 5% to about 95% by weight of the composition, in embodiments from about 20% to about 80% by weight of the composition.

As noted above, in embodiments the present compositions may contain one or more bioactive agents. The bioactive agent may be included within the formulation containing the biotin-containing component, the avidin-containing component, or both. The bioactive agent may be simply blended or mixed with the biotin-containing component, the avidin-containing component, or both, and stored as part of the component(s) until use. Alternatively, the bioactive agent can be mixed with the biotin-containing component and/or the avidin-containing component immediately prior to use. In other embodiments, the bioactive agent may be bound to the biotin-containing component, the avidin-containing component, or both. Combinations of the foregoing, e.g., where at least one bioactive agent is bound to one of the components as well as mixed or blended therewith, are also contemplated.

For example, in embodiments, a multifunctional polymer, such as polyethylene glycol, may possess some arms functionalized with biotin, with other arms functionalized with a bioactive agent. In embodiments, arms may be functionalized with both biotin and a bioactive agent, while other arms are just functionalized with biotin. Those arms possessing both biotin and a bioactive agent may first be functionalized with biotin, followed by attachment of the bioactive agent. In other embodiments, at least some of the arms of the PEG may be functionalized with a biotinylated bioactive agent.

By leaving some of the arms functionalized with just biotin, some portion of the biotin-containing component remains available to bind with avidin, thereby forming a composition of the present disclosure. The remaining arms of the macromer, possessing the bioactive agent, remain unreacted, permitting release of the bioactive agent in vivo. Crosslinking density and bioactive agent loading may be controlled through the ratio of the number of arms having biotin available to bind to avidin to the number of arms having bioactive agent.

As noted above, in embodiments, a bioactive agent may be included with an avidin-containing component. For example, one could functionalize avidin with a bioactive agent, or vice-versa, and then allow the avidin to bind to a PEG-biotin macromer. As avidin has 4 binding sites capable of binding biotin, multiple sites of the avidin could be functionalized with a bioactive agent, so long as at least one binding site is left free to bind to biotin. The avidin binding site may then bind to the biotin-containing component, thereby forming a composition of the present disclosure, with the bioactive agent released from the avidin-containing component by its cleavage from the avidin, or its hydrolysis from the hydrogel.

In embodiments, the release rates and total cumulative release may be influenced by the degree of substitution of bioactive agent on the biotin-containing component and/or the avidin-containing component.

In addition, as noted above, in embodiments at least a portion of the biotin-containing component, the avidin-containing component, or both, may include degradable and/or bioabsorbable elements capable of undergoing hydrolysis in vivo. Thus, where a bioactive agent is attached to a multifunctional component on an arm that includes a degradable and/or bioabsorbable element, the bioactive agent is released as the hydrolysable linkage degrades.

One type of bioactive agent could be included in a composition of the present disclosure, or a combination of bioactive agents could be included. For example, different arms of a multifunctional polymer possessing biotin arms could possess the same or different bioactive agents, more than one binding site of avidin could be functionalized with the same or different bioactive agents, multiple biotin-containing components could be conjugated to the same or different bioactive agents, and/or multiple avidin-containing components could be conjugated to the same or different bioactive agents.

As noted above, in embodiments, the biotin/avidin reaction forms a hydrogel. This composition of the present disclosure may, in embodiments, be used as a drug delivery vehicle. In other embodiments, the composition of the present disclosure thus formed may be added to other materials and/or precursors as a drug delivery component. In other embodiments, the composition of the present disclosure thus formed may be coated onto another device, such as a stent, mesh, implant, combinations thereof, and the like, and used as mechanism for the controlled delivery of a bioactive agent therefrom.

As noted above, a combination of different bioactive agents may be bound to either or both components used to form a hydrogel. Moreover, as also noted above, in some cases a bioactive agent may simply be mixed in with the components without being bound thereto. Combinations of the above, i.e., bioactive agents bound to one or both components, as well as bioactive agents simply mixed therewith, may also be used. For example, PEG macromers may be terminated in biotin, with some degree of substitution with biotinylated bioactive agent(s), which results in macromers having arms ending with both biotin and bioactive agent(s). Moreover, as noted above, avidin modified bioactive agent(s) may be included. Moreover, free bioactive agent(s), which may be soluble in solution and combined with the above components, but not reacted therewith, or insoluble drugs in suspension, may be combined with biotin/avidin components, without bonding thereto.

In embodiments, where bioactive agent(s) are included with a composition of the present disclosure by multiple mechanisms (i.e., both bound and mixed), the composition of the present disclosure may have various release rates of the bioactive agent(s) included therein. For example, in some embodiments, a bioactive agent not bound to the biotin-containing component or avidin-containing component, but merely mixed therewith, may be released more quickly than a bioactive agent bound to the biotin-containing component and/or avidin-containing component. Such a composition of the present disclosure may thus, in embodiments, have at least two release profiles of the bioactive agent.

Similarly, by selecting biotin-containing components and/or avidin-containing components with differing degradable linkages thereon, one could produce a composition of the present disclosure having multiple drug release profiles, which would be based upon both the release of a bioactive agent not bound to the biotin-containing component and/or avidin-containing component; the release of a bioactive agent bound to the biotin-containing component and/or avidin-containing component having a first degradable linkage; and the release of a bioactive agent bound to the biotin-containing component and/or avidin-containing component having a second degradable linkage. Such a composition of the present disclosure would have at least three release profiles of the bioactive agent(s). Moreover, different or additional degradable linkages may be utilized on the biotin-containing component, the avidin-containing component, or both, to arrive at additional release rates of the bioactive agents attached thereto.

Using these variable release systems, the same drug may be released over varying times, different drugs may be released over varying times, or both. In embodiments, a composition of the present disclosure may release from about 2 to about 6 different bioactive agents, in embodiments from about 3 to about 5 different bioactive agents.

The resulting composition of the present disclosure formed by the reaction of biotin with avidin may have the bioactive agent(s) included therein by various mechanisms. One mechanism for release of the bioactive agent(s) may be based on solubility and diffusion characteristics in the surrounding medium, e.g., its water solubility. If highly soluble in aqueous media, the bioactive agent will be rapidly released from the hydrogel. However if solubility is poor, release will be driven by its slow dissolution/solubility limit. In such a case, if the rate of dissolution is longer than the time for hydrolysis of any degradable linkages, that could be the longer delivery route.

Another mechanism for release of bioactive agent(s) from the composition of the present disclosure is the hydrolysis or degradation of any linkage binding the bioactive agent(s) to the biotin-containing component or the avidin-containing component.

Yet another mechanism for release of bioactive agent(s) from the composition of the present disclosure is the degradation/dissolution/hydrolysis of the composition of the present disclosure itself.

Thus, in embodiments, the individual release rates of bioactive agents may be based on cleavage from the components, and includes different degradable linkages having different release rates, degradation/dissolution of the avidin/biotin hydrogel, and subsequent drug release therefrom, and dissolution/diffusion of admixed free drug.

In embodiments, the time of release of a first bioactive agent may be from about 0 days to about 10 days, the time of release of a second bioactive agent may be from about 0 days to about 30 days, and the time of release of a third bioactive agent may be from about 0 days to about 180 days. In other embodiments, the time of release of a first bioactive agent may be form about 2 days to about 8 days, the release of a second bioactive agent may be from about 9 days to about 29 days and the release of a third bioactive agent may be from about 30 days to about 120 days. Moreover, while the above release rates refer to three different bioactive agents, as note above, the same bioactive agent could similarly be released at the three different rates to provide for sustained release of the agent.

Various combinations of the above drugs and different release profiles may be utilized. Thus, depending upon the condition to be treated, one could select the desired drug, determine the desired release rate of such drug, and then incorporate the drug in a composition of the present disclosure through physical or chemical incorporation, thereby achieving the desired rate of release from the composition of the present disclosure. Accordingly, a composition of the present disclosure could have various orders of release rates at distinct times, e.g., a first release of a first bioactive agent for a first period of time, followed by a second release of a second bioactive agent for a second period of time, followed by a third release of a third bioactive agent for a third period of time. The times of release could overlap, or the times of release could be distinct. For example, the composition could release a first bioactive agent for a first period of time, after which it releases a second bioactive agent over a second period of time, after which it releases a third bioactive agent over a third period of time, where the first period of time, the second period of time, and the third period of time do not overlap. Alternatively, a composition of the present disclosure could release multiple bioactive agents beginning at different points in time after implantation, for overlapping periods of time. For example, the composition could have a first release of a first bioactive agent, followed by a second release of a second bioactive agent, followed by a third release of a third bioactive agent, where the release of the first, second, and third bioactive agents, once begun, occurs for the remainder of the useful life of the composition of the present disclosure.

Drug delivery devices of the present disclosure may possess other varying release profiles, including varying orders of release. A drug delivery device of the present disclosure may include a first order of release, a second order of release, etc. For example, the drug delivery device could release a bioactive agent immediately upon implantation in a patient as a burst, while at the same time also having a sustained release of the same or different bioactive agent over time.

For example, for wound healing, it may be desirable to have a drug delivery device including a composition of the present disclosure initially release a hemostatic agent, anti-adhesion agent, or combinations thereof, followed by the release of an anti-inflammatory agent, followed by the release of an anti-scarring agent. For cardiac surgery, it may be desirable for a drug delivery device including a composition of the present disclosure to initially release an anti-adhesion agent, followed by a long-term release of an anti-arrhythmic agent.

The term "bioactive agent", as used herein, is used in its broadest sense and includes any substance or mixture of substances that may have clinical use. Alternatively a bioactive agent could be any agent that provides a therapeutic or prophylactic effect, a compound that affects or participates in tissue growth, cell growth or cell differentiation, a compound that may be able to invoke a biological action such as an immune response, or could play any other role in one or more biological processes.

Examples of classes of bioactive agents which may be utilized in accordance with the present disclosure include antimicrobial agents, proteins, peptides, antipyretic agents, antiphlogistic agents, analgesic agents, anti-inflammatory agents, vasodilators, antihypertensive agents, antiarrhythmic agents, hypotensive agents, antitussive agents, antineoplastic agents, local anesthetics, hormone preparations, antiasthmatic agents, antiallergic agents, antihistaminics, anticoagulants, antispasmodics, cerebral circulation improvers, metabolism improvers, antidepressants, antianxiety agents, vitamin D preparations, hypoglycemic agents, antiulcer agents, hypnotics, antibiotics, antifungal agents, sedative agents, bronchodilator agents, antiviral agents, dysuric agents, glycosaminoglycans, carbohydrates, nucleic acids, inorganic biologically active compounds, organic biologically active compounds, enzymes, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides. It is also intended that combinations of bioactive agents may be used in the present compositions. Bioactive agents herein also include all forms of the bioactive agent, including isomers, salt forms, and the like.

Suitable antimicrobial agents which may be included as a bioactive agent in the compositions of the present disclosure include triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent in the compositions of the present disclosure.

Other bioactive agents which may be included as a bioactive agent in the compositions of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; antiemetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the composition of the present disclosure include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; and protein agonists; nucleic acids such as antisense molecules, DNA, and RNA; oligonucleotides; and ribozymes; naturally occurring polymers, including proteins such as collagen and derivatives of various naturally occurring polysaccharides such as glycosaminoglycans; peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the composition of the present disclosure. Methods for incorporating enzymes into liposomes and/or microspheres are within the purview of those skilled in the art.

In embodiments, bioactive agents may include small molecule drugs (for analgesia/anesthesia, chemotherapy, antimicrobial, wound healing, etc.), large molecules (peptides, proteins, antibodies, growth factors, toxins, etc.), cell therapies (autologous, pooled, etc.), and/or combinations thereof. In some cases, the bioactive agent may be large molecule drugs.

A variety of optional ingredients may also be added to the compositions of the present disclosure. A phospholipid surfactant that provides antibacterial stabilizing properties and helps dispense other materials in the compositions may be added to the compositions of the present disclosure. Imaging agents such as iodine or barium sulfate, or fluorine, can also be combined with the compositions of the present disclosure to allow visualization of the surgical area through the use of imaging equipment, including X-ray, MRI, and CAT scan.

Once obtained, the biotin-containing component and the avidin-containing component can be combined to form compositions of the present disclosure which, in embodiments, may be utilized as a drug delivery device, or a biocompatible adhesive or sealant. In embodiments, the biotin-containing component and the avidin-containing component may be applied directly onto a tissue surface to form a three-dimensional crosslinked matrix as a result of the reaction between the biotin groups with the avidin groups.

Application of the present compositions, with or without other additives, can be done by any conventional means. These include dripping, brushing, or other direct manipulation of the composition on the tissue surface, or spraying of the biocompatible composition to the surface. In open surgery, application by hand, forceps, or the like is contemplated. In endoscopic surgery, the biocompatible composition can be delivered through the cannula of a trocar, and spread at the site by any device within the purview of those skilled in the art.

The biocompatible composition can also be dispensed from a conventional adhesive dispenser, which may provide mixing of the biotin-containing component and the avidin-containing component prior to dispensing. Such dispensers are disclosed, for example, in U.S. Pat. Nos. 4,978,336; 4,361,055; 4,979,942; 4,359,049; 4,874,368; 5,368,563; and 6,527,749, the entire disclosures of each of which are incorporated herein by reference. Thus, in embodiments, the present disclosure also relates to an apparatus that includes a first chamber containing a first composition containing a biotin-containing component, a second chamber containing a second composition containing an avidin-containing component, and one or more outlets for simultaneously dispensing the first and second compositions.

The biocompatible composition resulting from the mixture of the biotin-containing component and the avidin-containing component can be used in human and animal medical applications including, but not limited to, drug delivery, wound closure (including surgical incisions and other wounds), adhesives and/or coatings for medical devices (including implants), sealants and void fillers, and embolic agents. The biocompatible compositions can be used in a medical/surgical capacity in place of, or in combination with, sutures, staples, clamps and the like. Use of the present compositions can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

In some embodiments, the biocompatible composition can be used to seal or adhere delicate tissue together, such as lung tissue, in place of conventional tools that may cause mechanical stress. The use of a composition of the present disclosure as both an adhesive or sealant, as well as a drug delivery device, may be useful for the treatment of wounds, where the composition of the present disclosure provides both wound closure and enhanced healing due to the presence of the bioactive agents.

Additional applications of the biocompatible composition include sealing tissues to prevent or control blood, or other fluid leaks, at suture or staple lines. In another embodiment, the biocompatible composition can be used to attach skin grafts and position tissue flaps during reconstructive surgery. In still another embodiment, the biocompatible composition can be used to close tissue flaps in periodontal surgery. The resulting biocompatible composition can also be used to seal air and/or fluid leaks in tissue as well as to prevent post-surgical adhesions and to fill voids and/or defects in tissue. Alternatively, the present compositions can be cured into useful solid shapes such as, for example, anti-adhesion barriers, staple buttresses, suture pledgets, tissue bulking devices, and the like. The present compositions can also be applied as a biocompatible coating to any desired medical device.

To effectuate the joining of two tissue edges, the two edges are approximated, the biotin-containing component is combined with the avidin-containing component and applied to the approximated edges, and the two components crosslink with each other thereby forming the biocompatible composition of the present disclosure. In other embodiments, the biotin-containing component may be applied to one tissue edge, the avidin-containing component may be applied to a second tissue edge, and the two tissue edges approximated so that the biotin-containing component is combined with the avidin-containing component, and the two components crosslink with each other thereby forming the biocompatible composition of the present disclosure. The crosslinking reaction is rapid, generally taking less than one minute. In this case the composition of the present disclosure can be used as an adhesive to close a wound, including a surgical incision. In such a case, the composition of the present disclosure can be applied to the wound and allowed to set, thereby closing the wound. As noted above, bioactive agents which enhance would healing may be included in the composition of the present disclosure, thereby promoting wound healing.

In another embodiment, the biocompatible composition of the present disclosure may be used to adhere a medical device to tissue, rather than secure two edges of tissue. In some cases the medical device may include a coating of the biotin-containing component, the avidin-containing component, or both. In some aspects, the medical device includes an implant. Other medical devices include, but are not limited to, pacemakers, stents, shunts and the like. In embodiments, for adhering a device to the surface of animal tissue, the composition of the present disclosure, or the individual components thereof, can be applied to the device, the tissue surface or both. The device, biocompatible composition (or components thereof), and tissue surface are then brought into contact with each other and the composition is allowed to set, thereby adhering the device and surface to each other. Again, bioactive agents may be included to both promote healing and/or prevent implant rejection.

In other embodiments, one of the biotin-containing or avidin-containing components may be bound to an implant, such as a tissue engineered construct (e.g., foams, films, tissue scaffolds, pledgets, buttresses, and meshes), and the other component may be applied and bound to a tissue surface, thus providing the implant and tissue surface with a biotin or avidin rich surface. For example, a first precursor possessing tissue reactive groups could be applied to tissue and allowed to bind thereto, thus creating an avidin or biotin rich surface. An implant, having avidin when the first precursor has biotin, or having biotin when the first precursor has avidin, may then be placed in contact with the tissue, whereby the avidin-biotin affinity acts to adhere the implant to the tissue.

In embodiments, a collagen-based scaffold may be chemically reacted with the free amines of an avidin-containing component to covalently bind the avidin to the surface of the scaffold. The biotin-containing component may be bound to a tissue surface via tissue binding reactive groups, such as amine, carboxyl, or hydroxyl groups. The biotin may be directly conjugated to this reactive group or it may be attached by a linking agent as described above.

The implant may be placed in contact with of the tissue surface and the biotin-avidin affinity acts to adhere the implant to the tissue. As the binding is non-covalent, the implant may be removed and re-attached if not successfully positioned upon first contact, while still providing good tissue healing upon proper placement.

In another embodiment, in the case of cartilage repair, a hydroxy-reactive tissue binding end group may be linked to avidin to coat and adhere to subchondral bone. A biotinylated tissue scaffold could then be attached to the subchondral bone and affixed firmly in place, thereby preventing detachment by high loads and shear experienced in the joint.

In the case of breast reconstruction, an amine-reactive tissue binding end group may be linked to avidin to coat and adhere to an underlying tissue surface and to a skin flap. A biotinylated tissue scaffold (or mesh) may be positioned between to the underlying tissue surface and the skin flap such that the tissue scaffold (or mesh) acts like double-sided tape to adhere the underlying tissue and the skin flap, while also fostering tissue ingrowth and healing. In embodiments, the tissue scaffold may also be used for local delivery of pain medications, thereby also providing pain relief from the scaffold.

The present biocompatible composition can also be used to prevent post surgical adhesions. In such an application, the biocompatible composition may be applied and cured as a layer on surfaces of internal tissues in order to prevent the formation of adhesions at a surgical site during the healing process.

When used as a sealant, the biocompatible composition of the present disclosure can be used in surgery to prevent or inhibit bleeding or fluid leakage both during and after a surgical procedure. It can also be applied to prevent air leaks associated with pulmonary surgery. The biocompatible composition can be applied directly to the desired area in at least an amount necessary to seal off any defect in the tissue and seal off any fluid or air movement.

The present biocompatible composition has a number of advantageous properties. The resulting biocompatible compositions of the present disclosure are safe and biocompatible, possess enhanced adherence to tissue, are biodegradable, have enhanced hemostatic potential, have low cost, and are easy to prepare and use. By varying the selection of the polymer components, the strength and elasticity of the biocompatible composition can be controlled, as can the gelation time.

The biocompatible composition rapidly forms a compliant gel matrix, which ensures stationary positioning of tissue edges or implanted medical devices in the desired location and lowers overall required surgical/application time. The biocompatible composition exhibits little or no swelling upon gel matrix formation, and therefore retains the positional integrity of the aligned tissue edges and/or location of a medical device. The biocompatible composition forms strong cohesive bonds, based in part on the high affinity of biotin for avidin and/or streptavidin. It exhibits excellent mechanical performance and strength, while retaining the necessary pliability to adhere living tissue. This strength and pliability allows a degree of movement of tissue without shifting the surgical tissue edge. Additionally, the biocompatible composition is biodegradable, allowing the degradation components to pass safely through the subject's body.

It will be understood that various modifications may be made to the embodiments disclosed herein. Therefore the above description should not be construed as limiting, but merely as exemplifications of embodiments of the present disclosure. Those skilled in the art will envision other modifications within the scope and spirit of the claims appended hereto.

What is claimed is:

1. A drug delivery device comprising:
    a biocompatible biotin-containing component comprising a first polymer selected from the group consisting of polyethylene glycols and absorbable polymers, wherein the biotin-containing component has a molecular weight from about 500 Daltons to about 5000 Daltons;
    a biocompatible avidin-containing component comprising a polyethylene glycol; and
    at least one bioactive agent,
    wherein the absorbable polymer of the first polymer is selected from the group consisting of polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, polyglutamic acid, polyaspartic acid, poly(trimethylene carbonate), poly(iminocarbonate), copoly(ether-esters), polyalkylene oxalates, polyphosphazenes, polyiminocarbonates, aliphatic polycarbonates, and combinations thereof, and
    wherein the drug delivery device releases the at least one bioactive agent in vivo.

2. The drug delivery device of claim 1, wherein the biocompatible biotin-containing component comprises polyethylene glycol.

3. The drug delivery device of claim 1, wherein the biocompatible avidin-containing component is functionalized with avidin.

4. The drug delivery device of claim 1, wherein the biocompatible avidin-containing component is functionalized with streptavidin.

5. The drug delivery device of claim 1, wherein the at least one bioactive agent is selected from the group consisting of antimicrobial agents, proteins, peptides, antipyretic agents, antiphlogistic agents, analgesic agents, anti-inflammatory agents, vasodilators, antihypertensive agents, antiarrhythmic agents, hypotensive agents, antitussive agents, antineoplastic agents, local anesthetics, hormone preparations, antiasthmatic agents, antiallergic agents, antihistaminics, anticoagulants, antispasmodics, cerebral circulation improvers, metabolism improvers, antidepressants, antianxiety agents, vitamin D preparations, hypoglycemic agents, antiulcer agents, hypnotics, antibiotics, antifungal agents, sedative agents, bronchodilator agents, antiviral agents, dysuric agents, glycosaminoglycans, carbohydrates, nucleic acids, inorganic biologically active compounds, organic biologically active compounds, enzymes, angiogenic agents, anti-angiogenic agents, growth factors, antibodies, neurotransmitters, psychoactive drugs, anticancer drugs, chemotherapeutic drugs, drugs affecting reproductive organs, genes, oligonucleotides, and combinations thereof.

6. The drug delivery device of claim 1, further comprising at least one additional bioactive agent admixed with the biotin-containing component, the avidin-containing component, or both.

7. The drug delivery device of claim 6, wherein the additional bioactive agent admixed with the biotin-containing component, the avidin-containing component, or both, is the same as the bioactive agent.

8. The drug delivery device of claim 6, wherein the drug delivery device possesses from about 2 to about 6 different bioactive agents.

9. The drug delivery device of claim 6, wherein the drug delivery device comprises at least three drug release profiles comprising a first drug release profile of from about 0 days to about 10 days, a second drug release profile of from about 0 days to about 30 days, and a third drug release profile of from about 0 days to about 180 days.

10. The drug delivery device of claim 9, wherein the at least one bioactive agent released from the drug delivery device during the three drug release profiles is the same bioactive agent.

11. The drug delivery device of claim 9, wherein the first drug release profile is from about 2 days to about 8 days, the second drug release profile is from about 9 days to about 29 days, and the third drug release profile is from about 30 days to about 120 days.

12. The drug delivery device of claim 9, wherein the at least one bioactive agent released from the drug delivery device during the three drug release profiles comprises at least two different bioactive agents.

13. The drug delivery device of claim 9, wherein the at least one bioactive agent released from the drug delivery device during the three drug release profiles comprises three different bioactive agents.

14. The drug delivery device of claim 13, wherein a first bioactive agent is selected from the group consisting of hemostatic agents, topical anesthetics, anti-adhesion agents, antibiotics, and combinations thereof; a second bioactive agent is selected from the group consisting of analgesics, anti-inflammatories, anti-adhesion agents, antibiotics, and combinations thereof; and a third bioactive agent is selected from the group consisting of anti-cancer agents, anti-scarring agents, proteins, and combinations thereof.

15. The drug delivery device of claim 1, wherein the biotin-containing component is a biodegradable material.

16. The drug delivery device of claim 1, wherein the avidin-containing component is biodegradable.

* * * * *